US012484856B2

(12) United States Patent
Napier et al.

(10) Patent No.: US 12,484,856 B2
(45) Date of Patent: Dec. 2, 2025

(54) RECEIVE COIL FOR MRI BREAST IMAGING

(71) Applicant: FUJIFILM CORPORATION, Tokyo (JP)

(72) Inventors: Christophor Napier, Tallmadge, OH (US); Errol Brissett, Cleveland, OH (US); Dan DeLeon, Kent, OH (US); Mark Richard, Solon, OH (US)

(73) Assignee: FUJIFILM CORPORATION, Tokyo (JP)

(*) Notice: Subject to any disclaimer, the term of this patent is extended or adjusted under 35 U.S.C. 154(b) by 42 days.

(21) Appl. No.: 18/518,078

(22) Filed: Nov. 22, 2023

(65) Prior Publication Data

US 2025/0160758 A1 May 22, 2025

(51) Int. Cl.
*A61B 5/00* (2006.01)
*A61B 5/055* (2006.01)

(52) U.S. Cl.
CPC .............. *A61B 5/708* (2013.01); *A61B 5/055* (2013.01)

(58) Field of Classification Search
CPC ................................ A61B 5/708; A61B 5/055
See application file for complete search history.

(56) References Cited

U.S. PATENT DOCUMENTS

| | | | | |
|---|---|---|---|---|
| 7,482,809 B1 | 1/2009 | Shvartsman | | |
| 7,545,144 B2 | 6/2009 | Guan et al. | | |
| 8,285,361 B2 | 10/2012 | Guan et al. | | |
| 2010/0160810 A1* | 6/2010 | Parihar | A61B 90/11 | 600/562 |
| 2014/0213886 A1* | 7/2014 | Menon | A61B 5/708 | 600/411 |
| 2018/0132364 A1* | 5/2018 | Apter | F16M 11/041 | |
| 2024/0377487 A1* | 11/2024 | Greiser | G01R 33/34084 | |

* cited by examiner

*Primary Examiner* — Alexei Bykhovski
(74) *Attorney, Agent, or Firm* — Baker Botts L.L.P.

(57) ABSTRACT

An MRI support structure for imaging a breast region of a patient, said support structure comprising: a housing including a top portion, a bottom portion, a left support portion, and a right support portion wherein the top portion, bottom portion, and left support portion define a left cup opening, and the top portion, bottom portion, and right support portion define a right cup opening; a rail system comprising a plurality of rails each coupled to a bottom surface of the top portion; a lateral grid plate holder comprising a ratchet mechanism engaged with the rail system and configured to ratchet along the rail system in a medial direction; and a medial grid plate holder coupled to a top surface of the bottom portion.

24 Claims, 12 Drawing Sheets

RECEIVE COIL FOR MRI BREAST IMAGING

FIELD OF DISCLOSURE

The disclosed subject matter is directed to systems and methods for improving magnetic resonance imaging (MRI) systems, and particularly the imaging of patients' breasts with the use of MRI systems. The systems and methods described herein provide for improvements to the case of use of breast coil components.

DESCRIPTION OF RELATED ART

MRI is a medical diagnostic imaging technique used to diagnose many types of medical conditions. In MRI systems, three electromagnetic fields interact to produce images of anatomy, for example, human anatomy. The three fields include:

1) Main magnetic field—a static, spatially homogenous field to polarize spins of various nuclei within the body, making a net positive population available for detection. The static field must be very homogenous for imaging. For a horizontal field MRI system, the static magnetic field is oriented along the patient axis, or the head/foot direction of the patient. This axis is typically referred to as the Z-direction.
2) Gradient magnetic field—a spatially varying field that can create a difference in the z-component of the magnetic field across the imaging region. Additionally, the gradient magnetic field is switched at audio frequencies to encode spin positions and generate contrast. Practically, three spatially varying magnetic fields are created along the orthogonal axes to encode spins in three directions.
3) Radiofrequency (RF) magnetic field—a magnetic field operating at tens of MHz, used to add energy to spins, to detect the associated signals, and generate contrast. The direction of the RF field is orthogonal to the main magnetic field.

MRI systems can include a plurality of hardware components that work in conjunction with specialized software to produce the required magnetic fields and MRI images. MRI systems can include a main magnet, which can generate the main magnetic field, Bo. The main magnet of MRI systems can generate horizontal (aligned with the long axis (head-to-foot) of a patient laying on a horizontal table) or vertical (aligned from back to front of a patient laying on a horizontal table) magnetic fields. Most commonly, the magnetic field generated by the main magnet is 1.5 T or 3.0 T, but both lower and higher field strengths are also used clinically. Accordingly, the resulting physics for horizontal and vertical systems can be very different. Further, generalized descriptions of the operation of MRI systems can be found in U.S. Pat. Nos. 7,482,809 and 7,545,144, which are herein incorporated in their entirety.

The spins generated by the electromagnetic fields themselves generate an RF field, which can be received by an RF coil tuned to the nuclear magnetic resonance (NMR) frequency, which is proportional to the magnetic field. For MRI systems employing a 1.5 T magnet, this frequency is approximately 64 MHz. In order to maximize the NMR signal received, as well as to optimize the signal to noise, numerous receiving elements (channels) are typically implemented. As well, the receiving elements can be arranged as close to the anatomy of interest as possible. An MRI RF coil can employ solenoid elements, loop elements, saddle elements, or other shapes in order to maximize the received signal, while preventing cross-talk with other receive elements.

The disclosed subject matter relates to the RF Receive Coil, specifically for breast imaging, which can allow patients of various sizes to be accommodated, as well as methods to fixate devices for interventional procedures.

MRI breast imaging is most typically performed with the patient in the prone position, so that the breasts are in the pendulous position. As such, a structure is necessary to support the patient in the prone position. Existing structures are cumbersome and difficult to position at least due to their size and the presence of a spine coil, which is used to image patients' spine and which is generally fixed in place due to its own size.

Additionally, because biopsies of the breast are often performed while the patient is positioned in the MRI system, MRI imaging can be used in real time for needle guidance. Such insertion of said biopsy needle is typically done from the left or right side of the patient, as it is often impractical to access the breasts from either the head or the foot direction. Accordingly, access to the breasts is required from both the lateral and medial directions such that a biopsy needle can be inserted.

Grid plates can be utilized for such MRI-guided needle biopsies. The grid plates can allow the needle to be positioned in a known location and guided in a fixed direction. It can therefore be beneficial for the receive coil structure to be designed to hold these grid plates, and the grid plates to be able to move in a way that allows some amount of compression upon the breast in the medial direction. Additionally, since the grid plates are typically sterilized, it is desirous to have a method of loading the plate where the user need not touch items which are not sterile, thus contaminating the sterility of the grid plate(s).

Accordingly, there is a need for a breast coil support structure which can allow for easier setup and break down by MRI technicians.

SUMMARY

The purposes and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as the appended figures.

As embodied herein, an MRI support structure for imaging the breast region of a patient can include a housing, a rail system, a lateral grid plate holder, and a medial grid plate holder. The housing can include a top portion, a bottom portion, a left support portion, and a right support portion, wherein the top portion, bottom portion, and left support portion can define a left cup opening, and the top portion, bottom portion, and right support portion can define a right cup opening. The rail system can include a plurality of rails each coupled to a bottom surface of the top portion. The lateral grid plate holder can include a plurality of rails each coupled to a bottom surface of the top portion. The medial grid plate holder can be coupled to a top surface of the bottom portion.

As disclosed herein, each of the plurality of rails can include a plurality of rail teeth, and the ratchet mechanism can include a plurality of ratchet teeth which are configured to engage with the plurality of rail teeth. In some embodiments, the ratchet mechanism can further include a release mechanism having a latch and a push button, wherein the release mechanism can be in a lock position when the latch is engaged with the ratchet teeth, the release mechanism can be in a release position when the latch is disengaged from the ratchet teeth, and pushing the push button can move the release mechanism from the lock position to the release position. In yet another embodiment, the push button can be spring biased toward the lock position. As is also disclosed herein, the plurality of rails can include a first rail and a second rail, and the ratchet mechanism can include a first ratchet gear engaged with the first rail and a second ratchet gear engaged with the second rail. According to yet another embodiment, each of the plurality of rails can extend in a lateral-medial direction along each of a head side and a foot side of at least one of the left cup opening and the right cup opening. As is disclosed herein, the lateral grid plate holder can ratchet in a medial direction when the release mechanism is in the lock position. Furthermore, in another embodiment, the lateral plate holder can move freely in each of the medial direction and a lateral direction when the release mechanism is in the release position.

According to some embodiments, lateral grid plate can be moveable in a vertical direction. In some embodiments, a lock can prevent movement of the lateral grid plate holder in the vertical direction. In another embodiment, the medial grid plate holder can be connected at a pivot point to the bottom portion of the housing and can be configured to rotate at the pivot point relative to a vertical axis. In some embodiments, the medial grid plate holder can be disposed between the left cup opening and the right cup opening, and the lateral grid plate holder can be disposed at a lateral position relative to the medial grid plate holder.

The embodiments described herein also disclose a method for operating an MRI support structure for imaging a human breast region of a patient. The method can include laying an anterior side of the patient on a housing, positioning a medial grid plate holder at a medial position relative to a breast of the patient, positioning the breast of the patient within one of the left cup opening and the right cup opening, positioning a lateral grid plate holder at a lateral position relative to the breast, and compressing the breast between the medial grid plate and the lateral grid plate. The housing can include a top portion, a bottom portion, a left support portion, and a right support portion, wherein the top portion, bottom portion, and left support portion can define a left cup opening, and the top portion, bottom portion, and right support portion can define a right cup opening. The medial grid plate holder can hold a medial grid plate, and the lateral grid plate holder can hold a lateral grid plate. Compressing the breast can include ratcheting the lateral grid plate holder along a rail system in medial direction, and holding the medial grid plate holder in a static position.

As disclosed herein, the method can include activating a release mechanism to allow movement of the lateral grid plate holder in a lateral direction. In some embodiments, the release mechanism can include a latch positioned between a first ratchet tooth and a second ratchet tooth to prevent rotation of a ratchet gear in a direction, and activating the release mechanism can include removing the latch from between the first ratchet tooth and the second ratchet tooth such that the ratchet gear is allowed to rotate in the direction.

According to some embodiments, the method can include pivoting the medial grid plate holder relative to a vertical axis, and inserting a medial grid plate into the medial grid plate holder. In yet another embodiment, the method can include pivoting the medial grid plate holder up to approximately 30 degrees relative to the vertical axis.

DRAWINGS

FIGS. 1A-B show a perspective view of a breast coil and support structure.

FIG. 2 shows a perspective view of a lateral grid plate being held in a lateral grid plate holder.

FIGS. 3A-B show a ratchet mechanism for a lateral grid plate holder in each of a locked and released position, respectively.

FIGS. 4A-B show a medial grid plate holder in each of a vertical and angled position, respectively.

DETAILED DESCRIPTION

Figure 1A:
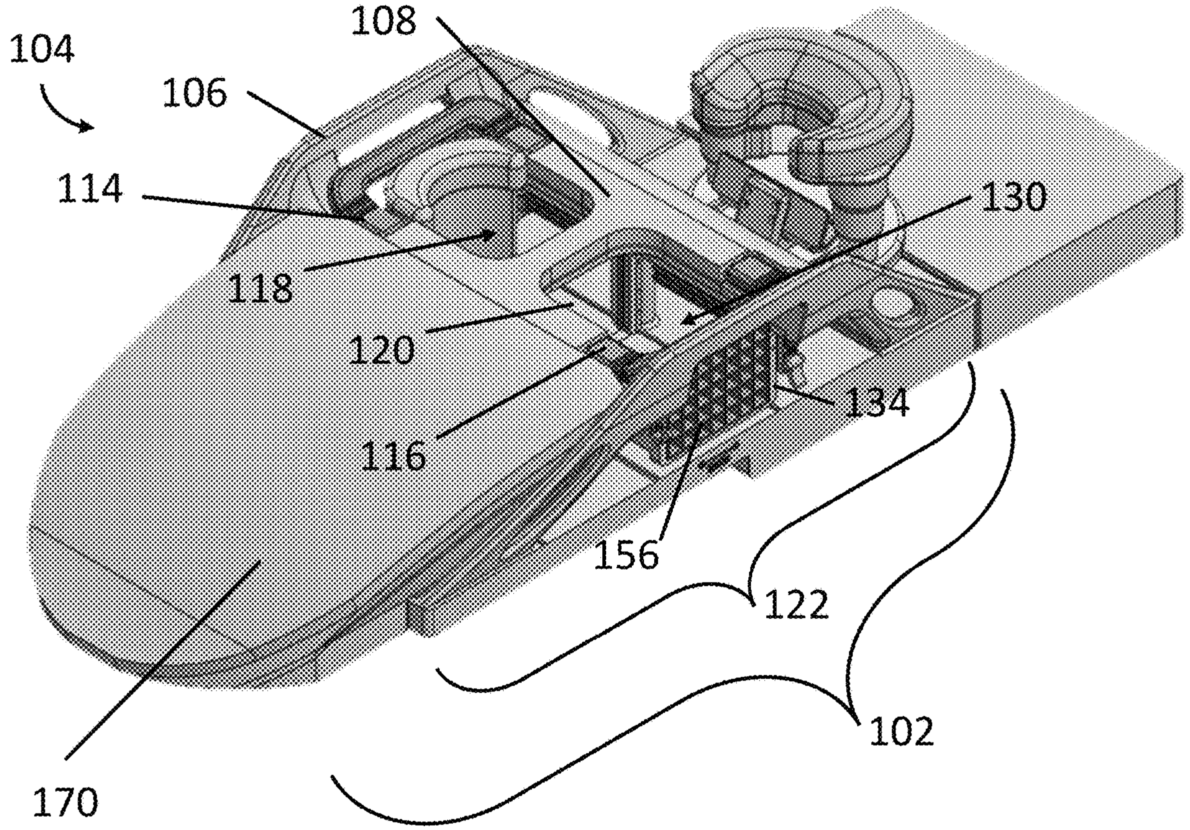

Reference will now be made in detail to various exemplary embodiments of the disclosed subject matter, exemplary embodiments of which are illustrated in the accompanying drawings. As used in the description and the appended claims, the singular forms, such as “a,” “an,” “the,” and singular nouns, are intended to include the plural forms as well, unless the context clearly indicates otherwise. In accordance with the disclosed subject matter, an MRI system for imaging a human breast region of a patient can include a breast coil which includes a housing and a receive coil. The housing can include a top portion, a bottom portion, a left support portion, and a right support portion such that the top portion, bottom portion, and left support portion define a left cup opening, and the top portion, bottom portion, and right support portion define a right cup opening. The bottom portion of the housing can include a first side and a second side. The first side can be adjacent a spine coil, the first side and the spine coil each being disposed on a tabletop. The second side can overlap a top surface of the spine coil such that a top surface of the bottom portion is approximately horizontal.

As is disclosed herein, the breast coil can include a ramp which is releasably coupled to the housing. The ramp can be at least partially disposed on the top surface of the spine coil. The ramp can be coupled to the housing with threaded fasteners. Alternatively, the ramp can include a protrusion mateable with a recess in the housing. As disclosed herein, the breast coil can include a lock to prevent the ramp from decoupling from the housing.

As disclosed herein, the breast coil can include at least one diagnostic paddle. The at least one diagnostic paddle can be configured to be releasably coupled to the receive coil by moving the at least one diagnostic paddle along a medial-lateral axis.

As disclosed herein, the first side of the bottom portion of the housing can include a channel configured to receive a cable extending from the spine coil.

In accordance with the disclosed subject matter, a method of operating an MRI system to image a human breast region of a patient can include providing a breast coil which includes a housing and a receive coil. The housing can include a top portion, a bottom portion, a left support portion, and a right support portion such that the top portion, bottom portion, and left support portion define a left cup opening, and the top portion, bottom portion, and right support portion define a right cup opening. The bottom portion of the housing can include a first side and a second side. The method can further include disposing, on a table-top, the first side of the bottom portion adjacent a spine coil, and overlapping a top surface of the spine coil with the second side of the bottom portion such that a top surface of the bottom portion is approximately horizontal.

The elements in the design of the breast coil are commonly formed using copper conductors, typically in the form of a flexible printed circuit board (PCB), as is known by one ordinarily skilled in the art. The elements can be constructed using a single PCB, or can be formed using multiple PCBs with copper jumpers or electrical components bridging adjacent sections to form a continuous signal path. The width, thickness and number of turns of copper conductor used are chosen for optimized sensitivity of the coil, as is commonly known in the art, and can vary depending on the individual system the coil is being used in conjunction with as well as the magnetic field strength of the MRI system. The elements can be, but are not necessarily, mounted on a frame structure to support the elements and ensure the elements are not bent or repositioned during imaging use of the coil. The frame structure can be constructed of a plastic material. At least a portion of the frame can be flexible enough to prevent cracking of the frame or elements during use of the coil, however should return to its original shape when the weight is removed. The design can also include electronic components in electrical connection with the elements of the design. These electronic components allow an efficient transfer of the received signal generated within the coil to the other components of the MR system to create the desired images of the patient.

Figure 1B:
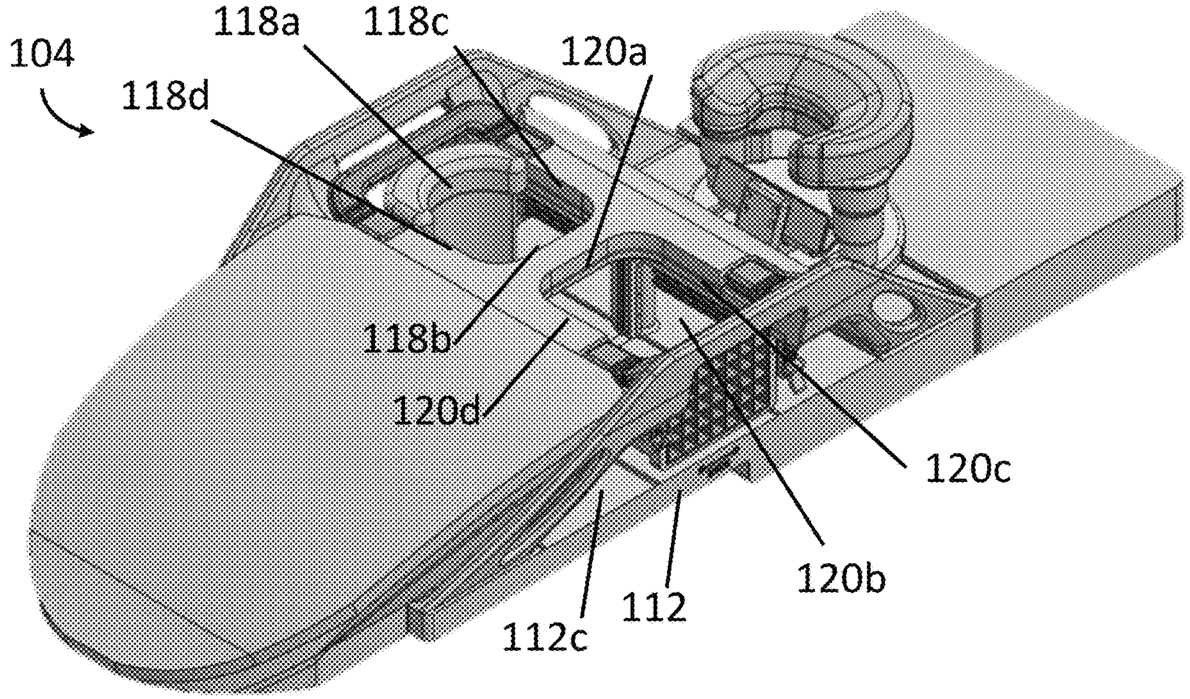

As illustrated in FIGS. 1A-B for purpose of illustration and not limitation, the design of breast coil 104 described herein includes housing 106 that includes a top portion 108 and a bottom portion 112. Bottom portion 112 of housing 106 can rest on the tabletop of the MRI system. Housing 106 can generally provide portions designed to contact and support the chest wall of the patient lying in the prone position on top of the coil design. Housing 106 can include two concave or cutaway portions designed to accept the patient's breasts, referred to herein as coil cups 118, 120. The coil cups 118, 120 can be defined by left side 118*a*, 120*a*, right side 118*b*, 120*b*, head side 118*c*, 120*c*, and foot side 118*d*, 120*d* and will be generally square or rectangular shaped. However, it is foreseen that the coil cups are not limited to a square or rectangular shape. The coil cups can be n-sided, or even circular. For the purposes of the present application, a coil having circular shaped cups will be seen as having an infinite number of sides, thus having more than the common four sides. It is also foreseen that coil cups 118, 120 can be enclosed on all sides except the top, or the coil cups can be generally open on the sides, such that no wall exists where no element is present.

Figure 8A:
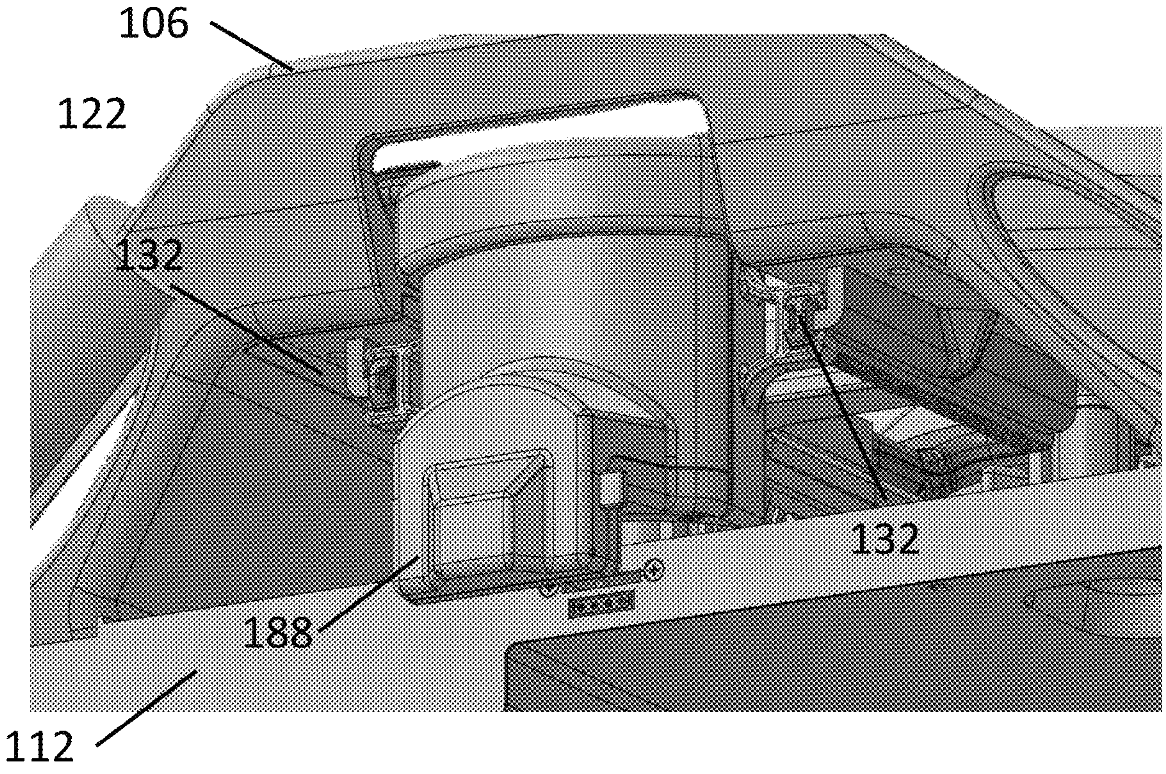
FIG. 8A shows a perspective view of a diagnostic paddle sliding in a lateral direction to be releasably coupled to a breast coil housing.

As is described in greater detail in U.S. Pat. No. 8,285,361, which is incorporated herein by reference in its entirety, the housing 106 can encase the individual coil elements disposed within the breast coil 104. The breast coil 104 in accordance with the disclosed subject matter will include loop elements surrounding each side of each of the coil cups 118, 120, two sets of saddle elements and counter rotating current (CRC) elements at the bottom of each cup 118, 120, and an element that spans the width of the coil 104, wrapping at least partially up both sides of the coil 104. The element that wraps up at least a portion of the sides of the coil can be enclosed in a rigid housing of the coil 104 or can be enclosed in a flexible housing that allows the element to be positioned at a closer distance to the patient being imaged in the coil. In general, it is possible to maximize the number of elements covering the anatomy to be imaged, so that the signal-to-noise ratio is maximized. However, the need to allow access to the anatomy for biopsy procedures or for positioning access requires a judicious choice of element locations. Those skilled in the art will realize that numerous element layout configurations can be selected. In accordance with the disclosed subject matter, a loop element can be located between the left and right cups 118, 120; two saddle elements and two CRC elements can also be located at the bottom of each cup 118, 120. Additionally, a loop element is located at the top surface of the left cup 118, extending through left support portion 114. Identically, a loop element is located at the top surface of the right cup 120, extending through the right support portion 116. Two CRC elements are located also at the top of the coil, one inferior to the breast cups 118, 120, and one superior to the breast cups 118, 120. Each of these two CRC elements extend the width of the coil in the left-right direction. As is shown in FIG. 8A and will be described in further detail below, some breast coils 104 can also include one or more diagnostic paddles 188 positioned on either or both of the left and right sides of the housing 106, wherein each of the diagnostic paddles can include an additional coil element disposed therein. As noted below, such diagnostic paddles 188 can be removably coupled to the breast coil 104 such that they are fixed in place when coupled to the breast coil 104. Again, those skilled in the art will recognize alternate element configurations are also possible.

In accordance with the disclosed subject matter, the breast coil design can be enclosed in a housing structure 106. While the housing structure 106 is not limited to any particular design, the housing structure 106 can be constructed of a combination of a rigid material, such as a hard plastic or polymer, and portions of the coil 104 can be constructed of a flexible material, such as a foam, rubberized polymer, or other similar material. There is no limitation, however, that the housing 106 must be entirely rigid, or partially flexible, as the housing can also be constructed solely from a rigid material such as a hard plastic. The housing 106 can be any material that can adequately protect the internal elements and associated electronics of the coil from any external pollutants such as moisture, dust and the like, with the only limitation being that the material used to construct the housing must not affect the MR images created by the coil 104, and also support the weight of the patient.

The housing 106 can be created from more than one type of material. For example, the housing 106 can be constructed from a rigid plastic, and also covered in a second material such as a vinyl or anti-microbial coating that allows for easy cleaning of the coil. Alternatively, a rigid housing integrated with a cushioning foam can be envisioned. Furthermore, a different material can be used to house the more sensitive electronics of the coil 104, such that while a rigid plastic and a flexible foam can be used for the main body of the coil housing, a different rigid plastic can be used to protect the electronics located at a centralized location of the coil 106. It is also foreseen that the electronics can be located in the same housing 106 as the coil 104 elements, below the coil 104 elements, between the MRI table and the elements, or elsewhere in the coil 104. The housing structure 106 can be shaped to conform with not only the design of the breast coil 104, but also to the general shape of the patient's chest and breast region to provide a comfortable fit during imaging of the patient.

The disclosed coil 104 can be used to image a significant majority of patients' breast and chest regions and does not require different sized coils 104 to obtain optimal imaging of patients. It is foreseen however, that a larger or smaller size coil 104 can be created using the designs disclosed herein to provide optimal imaging for very large or very small patients.

In addition to imaging, it can be desirable at times that a healthcare provider conduct a biopsy of the patient's breasts. It can also be desirable to use MRI imaging to guide the biopsy interventional instrument while conducting a biopsy of the patient's breasts. Therefore, the breast coil 104 and interventional instrument can be used in conjunction with one or more grid plates 154, 156, which are known in the art. Particularly, a grid plate 156 located on the lateral side of the patient's breast to be imaged can be moved in a medial direction to compress the patient's breast against a grid plate 154 located on the medial side of the patient's breast. In this way, the patient's breast can be more firmly held in place prior to receiving the interventional instrument to ensure accurate insertion. Furthermore, for the purpose of allowing the interventional instrument to pass through the grid plate 156 and to locate the interventional instrument in space, at least the lateral grid plate 156 can include a pattern of holes configured in a grid pattern. The grid plate pattern can be any suitable shape, for example squares, circles, or honeycomb. Either or both of the grid plates 154, 156 can also be replaced by a solid plate without a pattern of holes, so that compression can be applied to the breast. Generally, the clinician will utilize a grid plate 154, 156 on either the medial side or the lateral side of the breast undergoing a biopsy, and will utilize a solid plate on the alternate side such that compression and needle access can be obtained through the grid plate, and compression can be applied via a solid plate in the opposite direction.

Figure 3A:
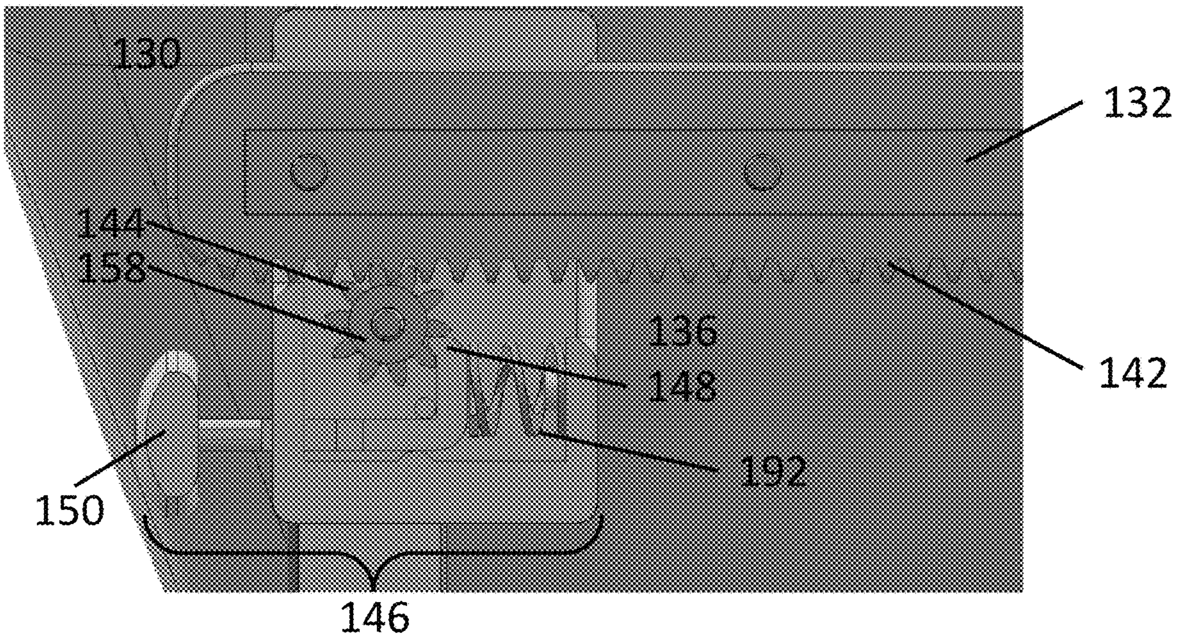

Accordingly, and as depicted in FIGS. 1A-B, an MRI support structure 102 for imaging a breast region of a patient is disclosed. The support structure 102 can include a housing 106, a rail system 130, a lateral grid plate holder 134, and (referring to FIGS. 4A-B) a medial grid plate holder 138. As described above, housing 106 can include a top portion 108 and a bottom portion 112, the top portion 108 including a left support portion 114 and a right support portion 116. Left support portion 114 can define a left cup opening 118 and the right support portion 116 can include a right cup opening 120, wherein each of the left and right cup openings 118, 120 can be defined by a left side 118*a*, 120*a*, a right side 118*b*, 120*b*, a head side 118*c*, 120*c*, and a foot side 118*d*, 120*d*, respectively. Furthermore, the rail system 130 can include (with reference to FIGS. 3A-B) a plurality of individual rails 132 wherein each of the individual rails 132 is coupled to a bottom surface 110 of the top portion 108 of the housing 106. The lateral grid plate holder 134 can include a ratchet mechanism 136 which engages with the rail system 130 to allow the lateral grid plate holder 134 to ratchet along the rail system 130 in a lateral-medial direction. To achieve this, each of the individual rails 132 can extend in the lateral-medial direction along each of the head side 118*c*. 120*c* and the foot side 118*d*, 120*d* of at least one of the left and right cup openings 118, 120. Additionally, the medial grid plate holder 138 can be coupled to a top surface 140 of the bottom portion 112 of the housing 106. It is envisioned that additional rails could be provided, for example directly below rail 132, to provide additional stability for the grid plate holder(s) 154, 156.

Figure 2:
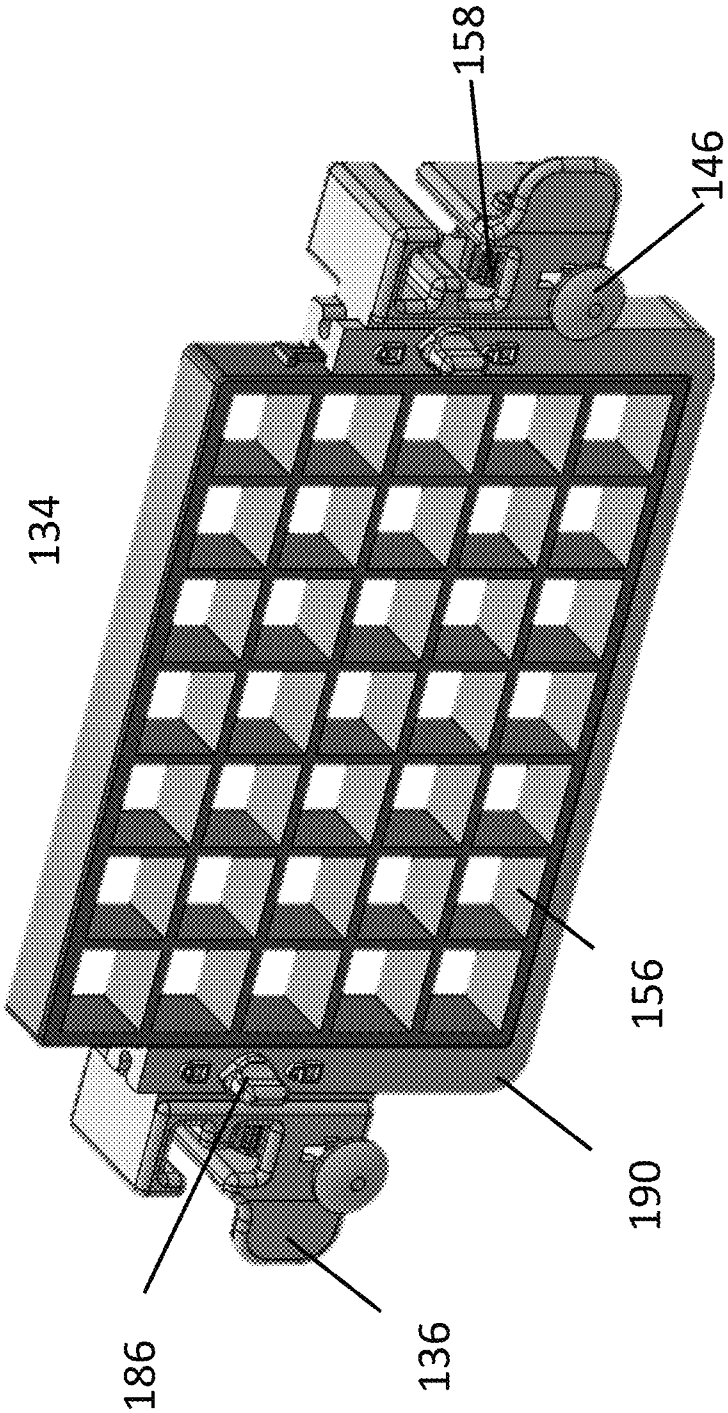
Figure 3B:
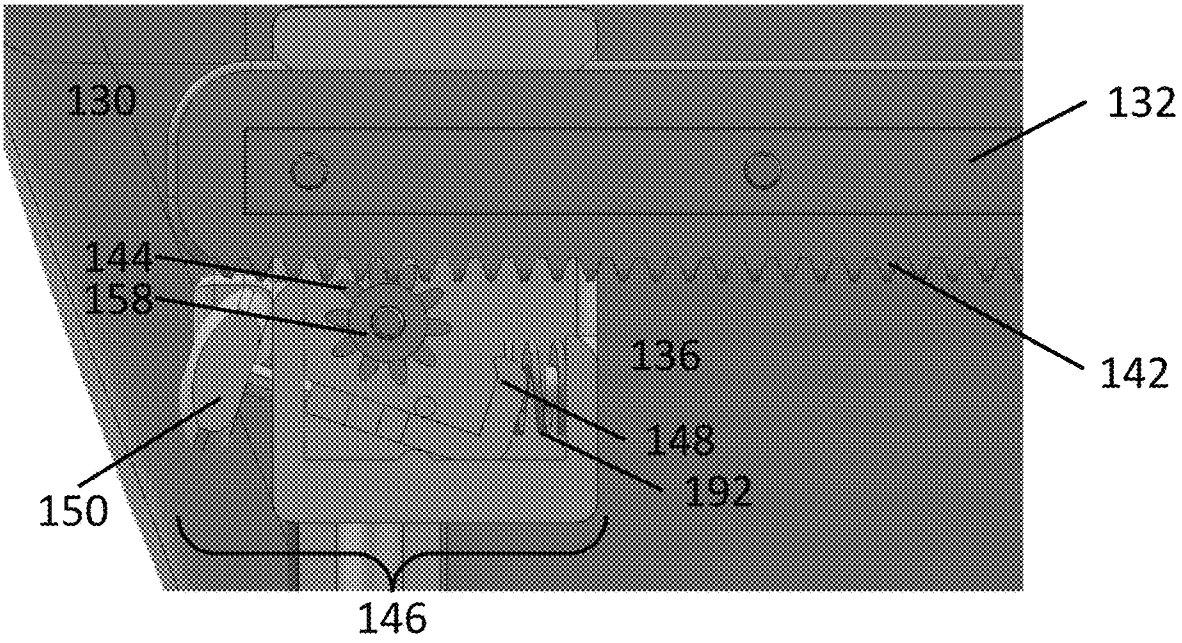

As shown in FIGS. 2-3B, the individual rails 132 and the ratchet mechanism 136 can each include teeth 142, 144 which engage with each other to allow movement of lateral grid plate holder 134 along the rails 132 in a lateral-medial direction. Furthermore, the ratchet mechanism 136 can include a release mechanism 146 which can be configured in a lock position or a release position. For example, the release mechanism 146 can include a latch 148 which engages with the ratchet teeth 144 of the ratchet gear 158—the ratchet teeth 144 being engaged with the rail teeth 142—such that the release mechanism 146 is in the lock position when the latch 148 is engaged with the ratchet teeth 144 and in the release position when the latch 148 is disengaged from the ratchet teeth 144. The release mechanism 146 can move from the lock position to the release position by pushing the push button 150. In this way, the push button 150 can be spring biased towards the lock position by spring 192 such that releasing the push button 150 causes the release mechanism 146 to move back from the release position to the lock position. By using ratchet mechanism 136, operators can more easily position lateral grid plate holder 134 and lateral grid plate 156. For example, the ratchet mechanism 136 can allow the operator to advance the lateral grid plate holder 134 and lateral grid plate 156 in the medial direction without inadvertent movement in the lateral direction. If the operator desires to move the lateral grid plate holder 134 and lateral grid plate 156 in the lateral direction, the release mechanism 146 can be easily moved from the lock position to the release position, thereby allowing movement in the lateral direction until the release mechanism 146 is returned to the lock position. Other suitable embodiments of the release mechanism will also be known to those skilled in the art; for example, the release mechanism can include a knob, a pull handle, an electromechanical assembly, or any other suitable embodiment.

Figure 5:
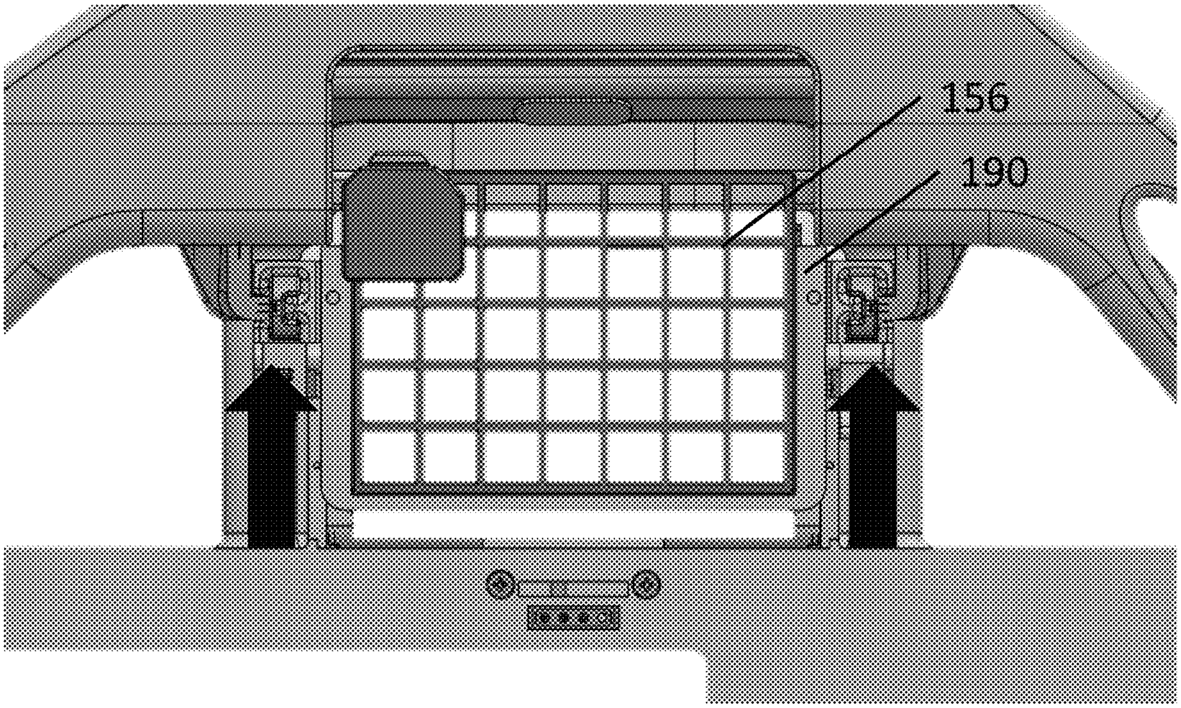
FIG. 5 shows a lateral grid plate and corresponding lateral grid plate holder being moved in a vertical direction.

As explained above, the lateral grid plate 156 serves the purpose of allowing an interventional instrument to pass through the lateral grid plate 156 while simultaneously compressing the patient's breast and locating the interventional instrument in space. Accordingly, it can become necessary to adjust the position of the lateral grid plate 156 to allow the interventional instrument to pass through the holes of the lateral grid plate 156 so that any area of the breast can be targeted for a biopsy. Therefore, the lateral grid plate holder base 190 can be configured to move in a vertical direction as is shown in FIG. 5. With reference now to FIG. 2, this can be achieved by sliding the medial grid plate base 190 vertically relative to the ratchet mechanism 136. For example, lateral grid plate holder base 190 and ratchet mechanism 136 can be mated with a dovetail joint to allow free movement of the lateral grid plate holder 190 in the vertical direction. To prevent unwanted vertical movement during an intervention procedure, the lateral grid plate holder base 190 can be locked in place by engaging lock 186. As can be seen in FIG. 2, in accordance with the disclosed subject matter, the lock 186 can be a twist or pull knob; however, one having skill in the art will understand that many other suitable embodiments may be possible.

Figure 4A:
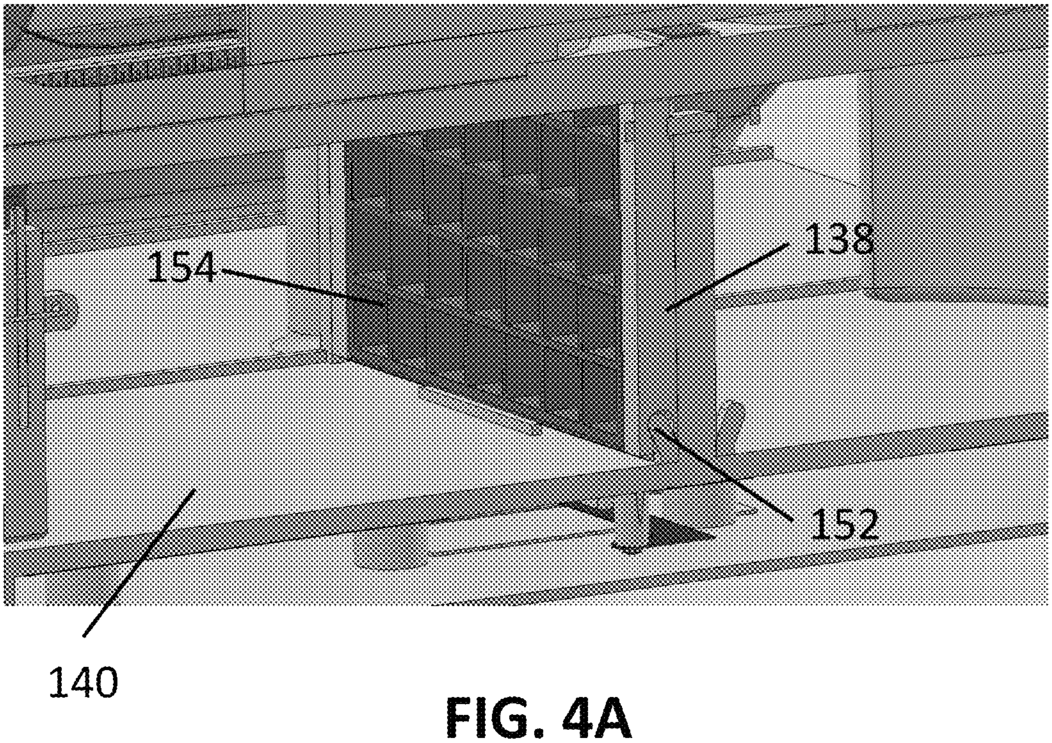
Figure 4B:
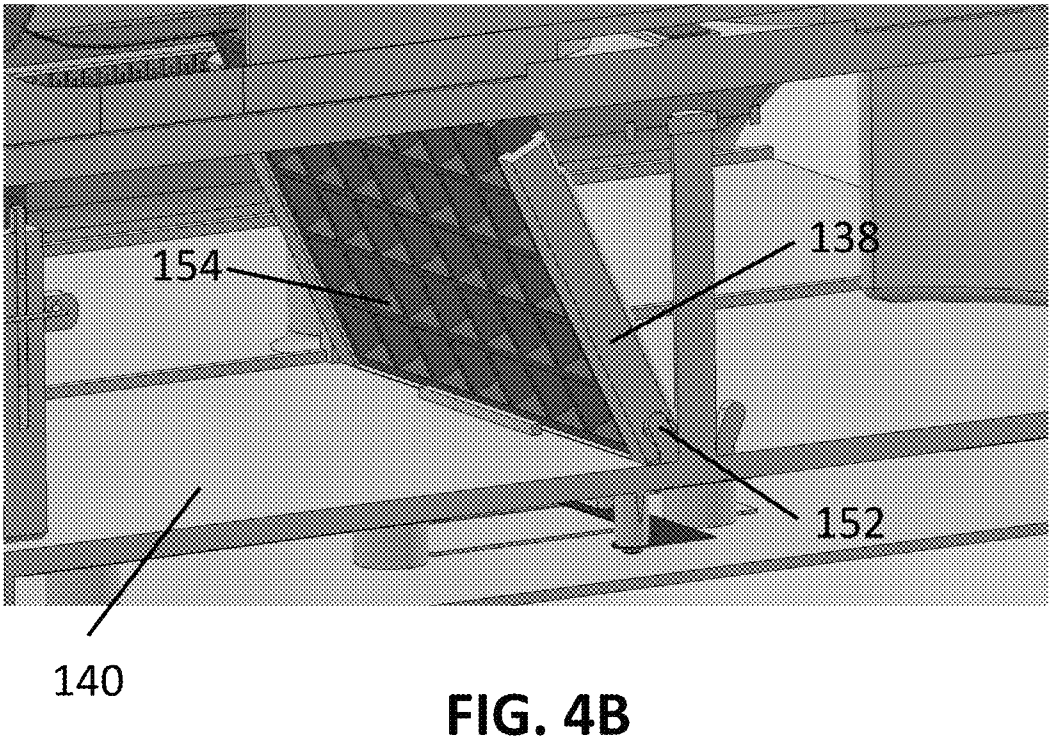

As is shown in FIGS. 4A-B, improvements to the medial grid plate holder 138 are also contemplated. Particularly, it is known that commercially available grid plates, including medial grid plates 154, are packaged in a sterile environment. For the health and well being of the patient, it is critical that this sterile environment is maintained. Accordingly, it is beneficial to minimize the physical contact between a healthcare provider and the medial grid plate 154. Separately, as has been disclosed and is shown in FIGS. 4A-B, in known breast coil systems the medial grid plates 154 are generally disposed between and underneath (with reference to FIGS. 1A-B) the left cup opening 118 and right cup opening 120; as such, loading the medial grid plate 154 into the medial grid plate holder 138 can be difficult and require disassembly of the housing 106, thus compromising the sterility of medial grid plate 158. To alleviate this, the medial grid plate holder 138 can be connected to the top surface 140 of (referring to FIG. 1B) the bottom portion 112 of the housing 106 at a pivot point 152. The top surface can also include two pivot points 152—one on each of the left and right sides—and the medial grid plate holder 138 can be transferred from one pivot point 152 to the other as needed. Alternatively, two separate medial grid plates 138 can be attached to each of the pivot points 152, respectively. Thus, by pivoting medial grid plate holder 138 relative to a vertical axis, medial grid plate 154 can be inserted into medial grid plate holder 138 through the left or right cup opening 118, 120, respectively, without the need for further disassembly of the housing 106. To properly position the medial grid plate holder 138 for insertion or removal of the medial grid plate 154, the medial grid plate holder 138 can be rotated approximately 30 degrees towards the respective cup opening 118, 120. Depending on the particular geometry of the housing 106, it can alternatively be necessary to rotate the medial grid plate holder 138 15 degrees, 45 degrees, or any other suitable angle. Additionally, either the medial grid plate holder 138 or the pivot point 152 can include a detent or any other suitable means to prevent unwanted rotation. Finally, to ensure proper functioning of the medial grid plate 154, the medial grid plate holder 138 can be disposed between the left and right cup openings 118, 120 and the lateral grid plate holder 134 can be disposed at a lateral position relative to the medial grid plate holder 138.

A method for operating an MRI support structure according to the above disclosure shall now be described. Particularly, the method can include laying the anterior side of a patient on a top portion 108 of a housing 106 as described above. Due to the patient's anterior side being positioned on the top portion 108, one of the patient's breasts can be positioned within one of the left and right cup opening 118, 120 as necessary. As is known in the art, the non-examined breast can, but need not, be supported by a blocker plate such that it is not positioned within the opposing cup opening 118, 120. The method can also include positioning the medial grid plate holder 138 holding a medial grid plate 154 at a medial position relative to the to-be-examined breast of the patient, and positing the lateral grid plate holder 134 holding a lateral grid plate 156 at a lateral position relative to the breast. Furthermore, to support the patient's breast, the breast can be compressed between the medial grid plate 154 and the lateral grid plate 156 by ratcheting the lateral grid plate holder 134 in a medial direction along the rail system 130, and holding the medial grid plate holder 138 in a static position.

After examination of the breast, or to adjust the compression of the breast, the release mechanism 146 can be activated to allow movement of the lateral grid plate holder 134 in a lateral direction. Furthermore, as explained above and with reference to FIGS. 3A-B, the release mechanism 146 can engage with ratchet teeth 144 such that it is positioned between two individual ratchet teeth 144 to prevent rotation of a ratchet gear 158 in either a clockwise or counter-clockwise direction; therefore, the method can further include activating the release mechanism 146 by removing the latch 148 from its position between the individual ratchet teeth 144 such that the ratchet gear 158 is allowed to rotate in one of the clockwise and counter-clockwise direction.

As is also explained above, and now with reference to FIGS. 4A-B, the medial grid plate 154 can be placed prior to the patient laying on the top surface 108. The medial grid plate holder 138 can be rotated, for example about 15 degrees, 30 degrees, 45 degrees, or other suitable angle relative to the vertical, and the medial grid plate 154 can be slide into the medial grid plate holder 138. After the medial grid plate 154 has been inserted, the medial grid plate holder 138 can be rotated back to vertical and the patient can lay on the top surface 108. Inserting the medial grid plate 154 into the medial grid plate holder 138 can occur prior to positioning the patient on the support structure 102, but can also occur after positioning the patient depending on the physical configuration of the structure 102.

As is well known. MRI systems are commonly used to image the spine and/or torso region of a patient. Like the breast coil, MRI systems typically use a specific RF receiving coil to image the spine, also known as a spine coil. Many commercially available spine coils have a generally rectangular form factor with a large length and width dimension sized to image a patient's spine and/or torso region, and a relatively small depth dimension. The resulting spine coil is thus large and cumbersome to move and, as a result, MRI technicians often leave the spine coil in place on its tabletop even when not in use. Accordingly, the case of operating the breast coil can be improved by providing a form factor which allows the breast coil to be used without needing to move a pre-positioned spine coil.

Figure 6A:
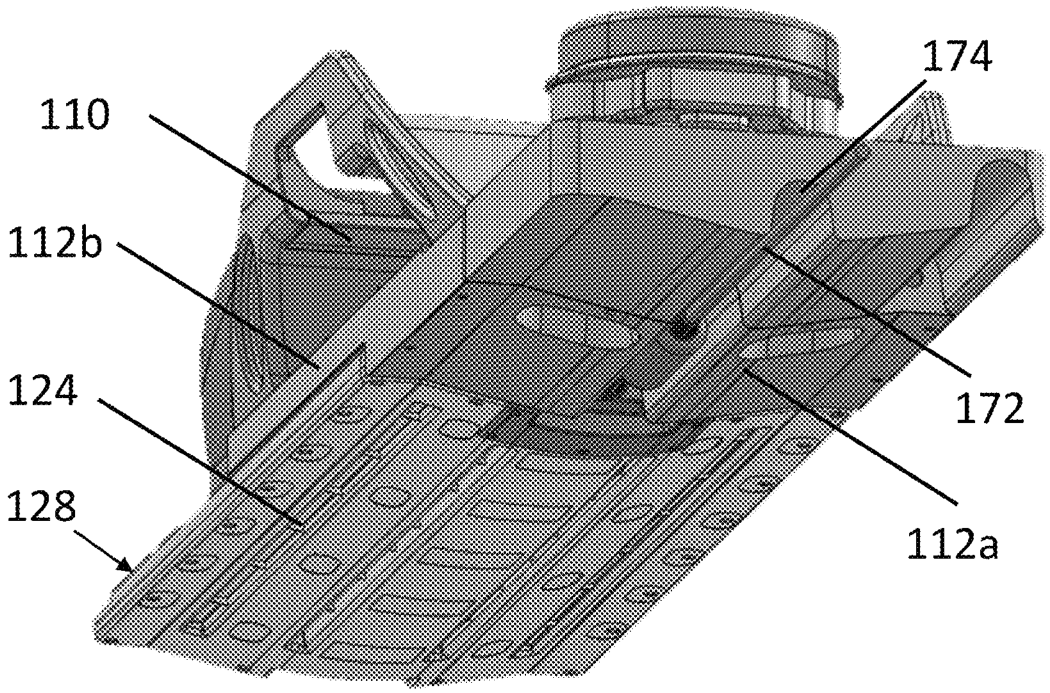
FIG. 6A shows a perspective view of a breast coil positioned adjacent a spine coil.
Figure 6B:
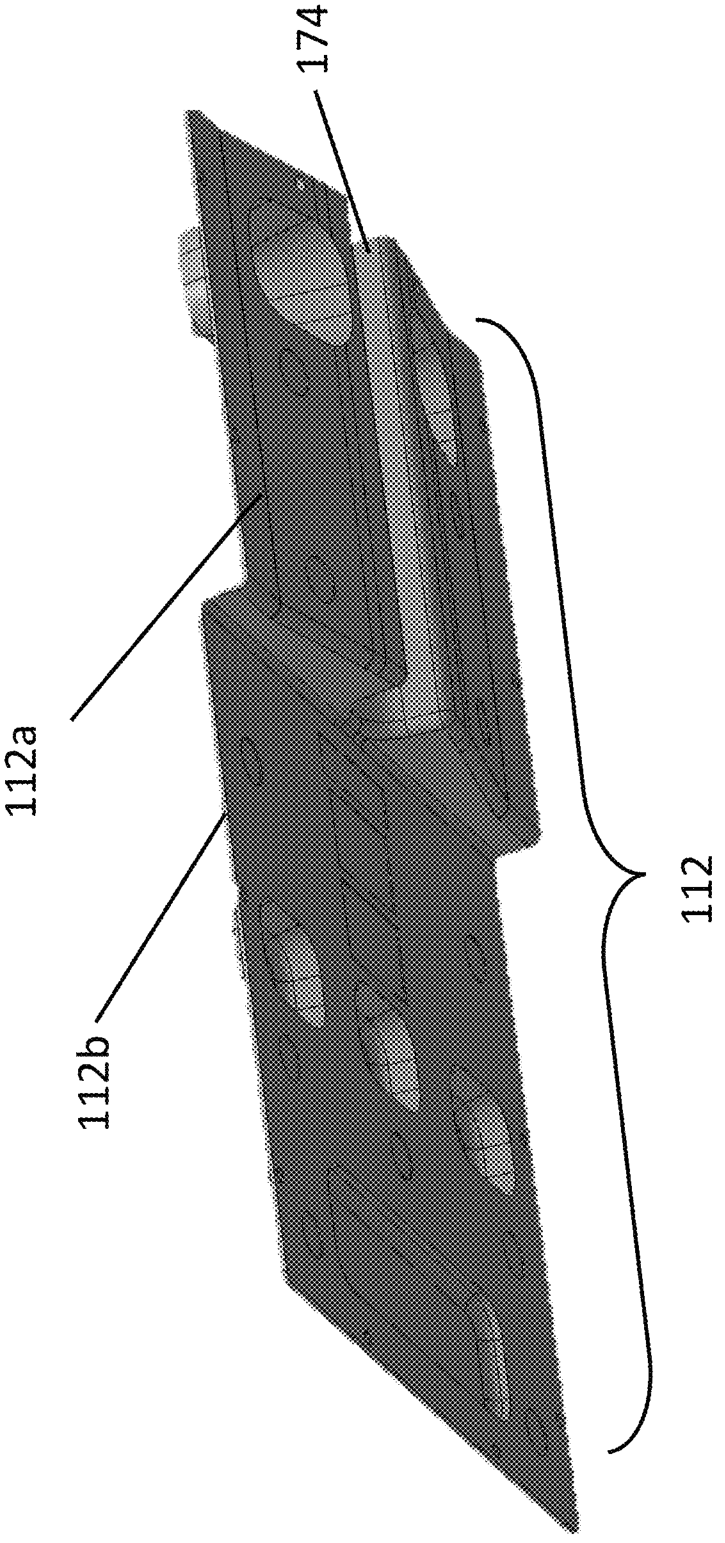
FIG. 6B shows a perspective view of a bottom portion of a breast coil housing.

To achieve these goals, an MRI system having a breast coil 104 for imaging a breast region of a patient is disclosed. The breast coil 104 can have each of the features described above with regard to FIG. 1, including support structure 102 having a housing 106 and a receive coil 122 configured to image the breast region of the patient. As explained above, housing 106 can include a top portion 108, a bottom portion 112, a left support portion 114, and a right support portion 116. Left support portion 114 can include a left cup opening 118 and the right support portion 116 can include a right cup opening 120, wherein each of the left and right cup openings 118, 120 can define a left side 118*a*, 120*a*, a right side 118*b*, 120*b*, a head side 118*c*, 120*c*, and a foot side 118*d*, 120*d*, respectively. Furthermore, (with reference to FIGS. 6A-B), bottom portion 112 can be shaped to overlap spine coil 124. For example and not limitation, the bottom portion 112 can include a first side 112*a* which is positioned adjacent spine coil 124 and a second side 112*b* which overlaps a top surface 128 of the spine coil 124 such that the top surface 112*c* of the bottom portion 112 is approximately horizontal. To achieve the correct alignment of the first side 112*a* and the spine coil 124, the first side 112*a* and the spine coil 124 can be mated in a lap joint configuration. Alternatively, the first side 112*a* and spine coil 124 can be mated in any suitable manner, for example and not limitation a tongue-and-groove configuration. As can be seen in FIGS. 6A-B, the first side 112*a* of the bottom portion 112 of the housing 106 can include a channel 174 which can receive the power and/or data cable 172 of the spine coil 124 to accommodate the adjacent placement of the breast coil 104.

Figure 7:
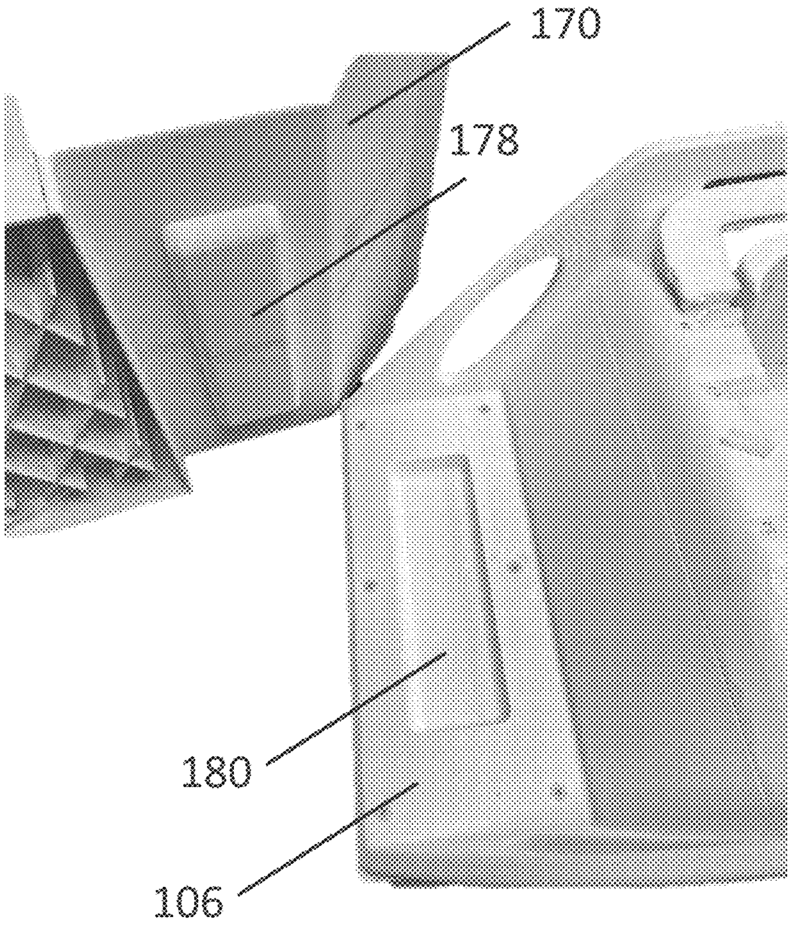
FIG. 7 shows a ramp capable of being releasably coupled to the breast coil housing.

As is shown in FIG. 7, to increase comfort for the patient, the breast coil 104 can further include a ramp 170 on the foot side of the housing 106. In accordance with the disclosed subject matter, the ramp 170 can be releasably coupled to the housing 106. This can be achieved in numerous suitable ways. For example, the ramp 170 can be mated to housing 106 with threaded fasteners, hooks, clips, or any other suitable fastener. Additionally or alternatively, the ramp 170 can include one of a protrusion 178 and a recess 180 which is mateable with a corresponding groove or protrusion 178, respectively, in the housing 106. For example and not limitation, the ramp 170 can have a 3-inch square protrusion 178 and the housing 106 can have a 3-inch square recess 180 such that when the protrusion 178 is positioned within the recess 180, the ramp 170 is prevented from moving in all but the vertical direction. In accordance with the disclosed subject matter, the ramp 170 can be partially positioned on the housing 106 and partially positioned on the top surface 128 of the spine coil 112. Alternatively, the ramp can be entirely positioned on either the top surface 128 of the spine coil 112 or entirely on the housing 106. As another example, the ramp 170 can be fixed to the breast coil 104.

In scenarios where a biopsy is not required to be performed, the accuracy and quality of the breast MRI image can be improved by increasing the number of RF receive coils use to image the patient's anatomy. As explained above, contained within the housing can be a plurality of coils to image the breast. However, due to the form factor of the housing, it may not be possible to adequately image the patient's breast from the lateral side. Accordingly, when an interventional instrument is not in use, a removable lateral RF receive coil—also referred to as a diagnostic paddle—can be positioned on the left and/or right side of the breast coil. To achieve this, the diagnostic paddle can be releasably coupled—mechanically and/or electrically—to the left and/or right side of the breast coil respectively.

Figure 8B:
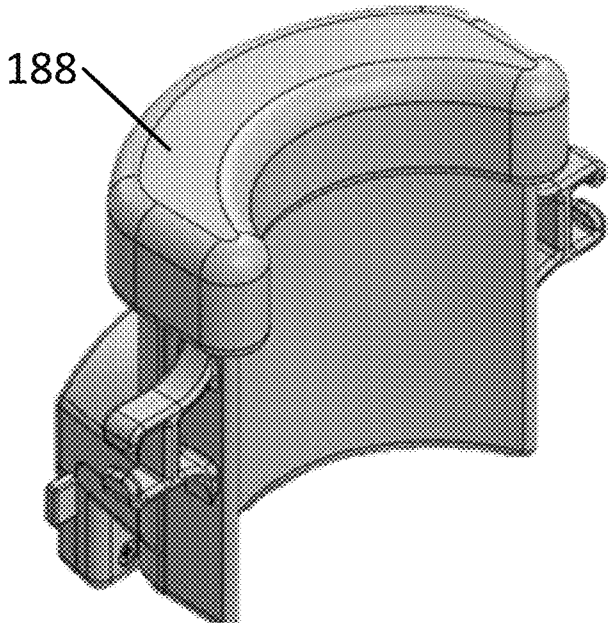
FIG. 8B shows a perspective view of a diagnostic paddle.
Figure 8C:
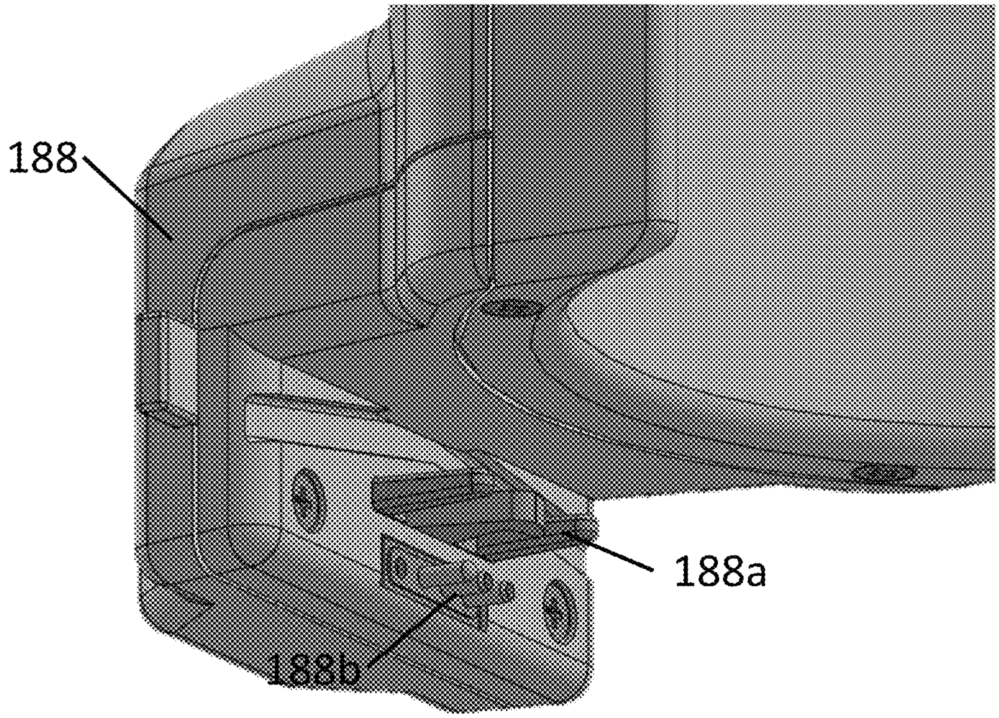
FIG. 8C shows a close-up view of the mechanical and electrical connectors of the diagnostic paddle.

Accordingly, as is shown in FIGS. 8A-C, the breast coil 104 (referring to FIG. 1A) can include at least one diagnostic paddle 188; specifically, the breast coil 104 can utilize a diagnostic paddle 188 on only the side corresponding to the breast to be imaged, or the breast coil 104 can utilize a diagnostic paddle 188 on each of the left and right side of the breast coil 104. To allow interchanging between the diagnostic paddle 188 and an interventional instrument, the at least one diagnostic paddle 188 can be releasably coupled to the housing 106. As an example, this can be achieved by directing the diagnostic paddle 188 along the medial-lateral axis until the mechanical and electrical connectors 188*a*, 188*b* of the diagnostic paddle 188 releasably mate with corresponding connectors located on the bottom portion 112 of the housing 106. Alternatively, the connectors can be disposed at any other suitable location of the breast coil 104. Furthermore, as is shown in FIG. 8A, the rails 132 can be used to support diagnostic paddle 188 and to assist in positioning the paddle 188 in space. Notably, and as shown in FIGS. 8A-B, the diagnostic paddle 188 need not engage with the rail teeth 142 depicted in FIGS. 3A-B and can simply slide over the rails 132. In an alternate embodiment an LED on the lateral surface of the diagnostic paddle can illuminate when the mechanical and electrical connections of the diagnostic paddle 188 to the breast coil 104 are completed, thus providing positive indication that the connection is complete.

According to the disclosures herein, a method for operating an MRI system to image a human breast region of a patient is also contemplated. For example, the method can include providing a breast coil 104 according to the embodiments disclosed herein. The method can further include disposing, on a tabletop, the first side 112*a* of the bottom portion 112 and a spine coil 124, the first side 112*a* being adjacent the spine coil 124. As is described above, the top surface 128 of the spine coil 112 can be overlapped by the second side 112*b* of the bottom portion 112 such that the top surface 112*e* of the bottom portion 112 is approximately horizontal.

As is described above, the method can also include releasably coupling the ramp 170 to the housing 106, which can be accomplished with either a threaded fastener, by mating a corresponding groove and recess, or by any other suitable means. As is also described above, it can be desirable to use the breast coil 106 in conjunction with diagnostic paddle 188. Accordingly, the method can further include releasably coupling at least one diagnostic paddle 188 to the receive coil 122 by moving the at least one diagnostic paddle 188 along the medial-lateral axis.

As is explained above, the breast coil 104 can be formed to be used without needing to remove the spine coil 124 from the MRI system when the spine coil 124. To achieve this, the tabletop can be comprised of a first tabletop portion coupled to a second tabletop portion, and the method includes placing the first side 112*a* of the bottom portion 112 of the housing 106 on the first tabletop portion, placing the spine coil 124 on the second tabletop portion, and positioning the first tabletop portion adjacent the second tabletop portion. To join the first and second tabletop portions, the first tabletop portion can include a first connector in electrical communication with the breast coil 104 and the second tabletop portion cab include a second connector which is mateable with the first connector. In this way, the breast coil 104 can utilize cable 172 of the spine coil 124 to transmit electrical power and/or data. Therefore, the method can include routing cable 172 through channel 174. More specifically, the spine coil 124 can connect to the breast coil 104 via a connector on the patient tabletop without the use of a cable, or the spine coil cable 172 can extend and connect to the MRI system in the opposite direction from the breast coil 104. Because the spine coil 124 and the breast coil 104 can both be present during a breast MRI examination, but are not generally used to image anatomy simultaneously, it is also possible for the breast coil 104 to utilize a mating connector to the spine coil such that the power to the breast coil 104, and the MRI signals from the breast coil 104, are routed into the spine coil 124 and then subsequently to the MRI system.

While the disclosed subject matter is described herein in terms of certain exemplary embodiments, those skilled in the art will recognize that various modifications and improvements can be made to the disclosed subject matter without departing from the scope thereof. Moreover, although individual features of one embodiment of the disclosed subject matter may be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A magnetic resonance imaging (MRI) support structure for imaging a breast region of a patient, said support structure comprising:
- a housing including a top portion, a bottom portion, a left support portion, and a right support portion wherein
  - the top portion, bottom portion, and left support portion define a left cup opening; and
  - the top portion, bottom portion, and right support portion define a right cup opening;
- a rail system comprising a plurality of rails each coupled to a bottom surface of the top portion;
- a lateral grid plate holder comprising a ratchet mechanism engaged with the rail system and configured to ratchet along the rail system in a medial direction, wherein a lateral grid plate held in the lateral grid plate holder is moveable in a vertical direction; and
- a medial grid plate holder coupled to a top surface of the bottom portion.

2. The support structure of claim 1, wherein each of the plurality of rails comprises a plurality of rail teeth and the ratchet mechanism comprises a plurality of ratchet teeth configured to engage with the plurality of rail teeth.

3. The support structure of claim 2, wherein the ratchet mechanism further comprises a release mechanism comprising a latch and a push button, and wherein:
- the release mechanism is in a lock position when the latch is engaged with the ratchet teeth;
- the release mechanism is in a release position when the latch is disengaged from the ratchet teeth; and
- pushing the push button moves the release mechanism from the lock position to the release position.

4. The support structure of claim 3, wherein the push button is spring biased toward the lock position.

5. The support structure of claim 1, wherein the plurality of rails comprises a first rail and a second rail, and the ratchet mechanism comprises a first ratchet gear engaged with the first rail and a second ratchet gear engaged with the second rail.

6. The support structure of claim 1, wherein the medial grid plate holder is connected at a pivot point to the bottom portion of the housing and is configured to rotate at the pivot point relative to a vertical axis.

7. The support structure of claim 1, wherein each of the plurality of rails extends in a lateral-medial direction along each of a head side and a foot side of at least one of the left cup opening and the right cup opening.

8. The support structure of claim 1, wherein
- the medial grid plate holder is disposed between the left cup opening and the right cup opening; and
- the lateral grid plate holder is disposed at a lateral position relative to the medial grid plate holder.

9. A method of operating a magnetic resonance imaging (MRI) support structure for imaging a human breast region of a patient, the method comprising:
- laying an anterior side of the patient on a housing including a top portion, a bottom portion, a left support portion, and a right support portion wherein the top portion, bottom portion, and left support portion define a left cup opening; and the top portion, bottom portion, and right support portion define a right cup opening;
- positioning a medial grid plate holder at a medial position relative to a breast of the patient, the medial grid plate holder holding a medial grid plate;
- positioning the breast of the patient within one of the left cup opening and the right cup opening;
- positioning a lateral grid plate holder at a lateral position relative to the breast, the lateral grid plate holder holding a lateral grid plate; and
- compressing the breast between the medial grid plate and the lateral grid plate, wherein compressing the breast comprises:
  - ratcheting the lateral grid plate holder along a rail system in a medial direction;
  - holding the medial grid plate holder in a static position; and
- activating a release mechanism to allow movement of the lateral grid plate holder in a lateral direction;
- wherein the release mechanism comprises a latch positioned between a first ratchet tooth and a second ratchet tooth to prevent rotation of a ratchet gear in a direction, and activating the release mechanism comprises removing the latch from between the first ratchet tooth and the second ratchet tooth such that the ratchet gear is allowed to rotate in the direction.

10. The method of claim 9, further comprising:
- pivoting the medial grid plate holder relative to a vertical axis; and
- inserting a medial grid plate into the medial grid plate holder.

11. The method of claim 10, further comprising pivoting the medial grid plate holder up to approximately 30 degrees relative to the vertical axis.

12. A magnetic resonance imaging (MRI) support structure for imaging a human breast region of a patient, said support structure comprising:
- a housing comprising a top portion and a bottom portion;
- a rail system connected to the bottom portion of the housing, the rail system comprising a plurality of rails oriented in a lateral-medial direction, each of the plurality of rails comprising a plurality of rail teeth; and
- a lateral grid plate holder comprising a plurality of ratchets configured to engage with each of the plurality of rails, respectively, each of the ratchets comprising:
  - a ratchet gear having ratchet teeth engaged with the rail teeth; and
  - a release mechanism comprising a latch and a push button, wherein:
    - the release mechanism is in a lock position when the latch is engaged with the ratchet teeth;
    - the release mechanism is in a release position when the latch is disengaged from the ratchet teeth; and
    - pushing the push button moves the release mechanism from the lock position to the release position-;
- wherein a lateral grid plate held by the lateral grid plate holder is moveable in a vertical direction.

13. The support structure of claim 12, wherein the lateral grid plate holder ratchets in a medial direction when the release mechanism is in the lock position.

14. The support structure of claim 13, wherein the lateral plate holder moves freely in each of the medial direction and a lateral direction when the release mechanism is in the release position.

15. The support structure of claim 14, wherein the push button is spring biased toward the lock position.

16. The support structure of claim 12, further comprising a lock to prevent movement of the lateral grid plate holder in the vertical direction.

17. A magnetic resonance imaging (MRI) support structure for imaging a breast region of a patient, said support structure comprising:

a housing including a top portion, a bottom portion, a left support portion, and a right support portion wherein the top portion, bottom portion, and left support portion define a left cup opening; and the top portion, bottom portion, and right support portion define a right cup opening;

a rail system comprising a plurality of rails each coupled to a bottom surface of the top portion wherein each of the plurality of rails extends in a lateral-medial direction along each of a head side and a foot side of at least one of the left cup opening and the right cup opening;

a lateral grid plate holder comprising a ratchet mechanism engaged with the rail system and configured to ratchet along the rail system in a medial direction; and a medical grid plate holder coupled to a top surface of the bottom portion.

18. The support structure of claim 17, wherein each of the plurality of rails comprises a plurality of rail teeth and the ratchet mechanism comprises a plurality of ratchet teeth configured to engage with the plurality of rail teeth.

19. The support structure of claim 18, wherein the ratchet mechanism further comprises a release mechanism comprising a latch and a push button, and wherein:

the release mechanism is in a lock position when the latch is engaged with the ratchet teeth;

the release mechanism is in a release position when the latch is disengaged from the ratchet teeth; and pushing the push button moves the release mechanism from the lock position to the release position.

20. The support structure of claim 19, wherein the push button is spring biased toward the lock position.

21. The support structure of claim 17, wherein the plurality of rails comprises a first rail and a second rail, and the ratchet mechanism comprises a first ratchet gear engaged with the first rail and a second ratchet engaged with the second rail.

22. The support structure of claim 17, wherein a lateral grid plate is moveable in a vertical direction.

23. The support structure of claim 17, wherein the medical grid plate holder is connected at a pivot point to the bottom portion of the housing and is configured to rotate at the pivot point relative to a vertical axis.

24. The support structure of claim 17, wherein the medical grid plate holder is disposed between the left cup opening and the right cup opening; and the lateral grid plate holder is disposed at a lateral position relative to the medical grid plate holder.

* * * * *